United States Patent [19]

Clayman

[11] Patent Number: 4,629,158

[45] Date of Patent: Dec. 16, 1986

[54] DISPOSABLE MALE VALVE MEMBER

[76] Inventor: Henry Clayman, 12555 Biscayne Blvd., Miami, Fla. 33181

[21] Appl. No.: 646,215

[22] Filed: Aug. 31, 1984

[51] Int. Cl.$^4$ .............................................. F16K 51/00
[52] U.S. Cl. .................................... 251/148; 251/142; 604/31; 604/34; 285/24; 285/38
[58] Field of Search ........ 251/142, 148, 297, 343–345; 604/19, 27, 30–34, 119; 285/24; 128/760, DIG. 27, DIG. 24, 274, 276, 350 R; 137/315

[56] References Cited

U.S. PATENT DOCUMENTS

| | | | |
|---|---|---|---|
| 3,416,567 | 12/1968 | Von Dardel et al. | 604/34 X |
| 3,833,013 | 9/1974 | Leonard | 604/31 X |
| 4,246,932 | 1/1981 | Raines | 604/30 X |
| 4,418,944 | 12/1983 | Haines et al. | 285/24 |

Primary Examiner—Larry Jones
Attorney, Agent, or Firm—Cushman, Darby & Cushman

[57] ABSTRACT

A male valve member for disposable use with a female member in a fluid T coupling in which a first bore extends from an inlet to outlet and a second bore communicates the first bore with a fluid flow opening in the female member. A sleeve preferably extends in the first bore to cover the opening of the second bore into the first bore to form a one-way valve. The valve member preferably includes parts at least which are resilient and positively lock the male and female members together upon insertion.

11 Claims, 4 Drawing Figures

DISPOSABLE MALE VALVE MEMBER

BACKGROUND AND SUMMARY OF THE INVENTION

The invention relates to a valve and to a male valve member for cooperation with a female member to form a fluid T coupling.

Valves for forming fluid T couplings are used in a variety of different applications. One of the most important of those applications is in surgical aspirators which are used to remove fluid from a body during surgery. Typically, the valve is formed of a male and female member with the female member being mounted on a housing which similarly mounts a pump and includes the various necessary control and electronic elements. Such valves and associated equipment are described in greater detail in U.S. Pat. No. 4,418,944.

In this arrangement, the female member has a generally cylindrical receptacle with a fluid flow opening into the receptacle for providing pressure relief to the T coupling upon command. The male member and attached inlet and outlet tubing are preferably supplied as a sterile unit and can be either disposable or reusable After each operation, the male member and tubing are removed, discarded, and replaced with a fresh sterile unit. Each such male member is formed with a first bore extending between the inlet and outlet tubes and a second bore communicating the first bore to the fluid flow opening of the female member to provide pressure relief. Normally the fluid flowing is air although some liquid may be entrained if present. A one-way valve is normally provided either in the female member or within the housing for preventing fluid flow through the second bore and into the housing and limiting flow through the second bore to pressure relief.

Some moisture, however, inevitably finds its way into the fluid flow opening of the non-disposable female member and the passageway between the one-way valve and that fluid flow opening Since the fluid is removed from the body during a surgical procedure, it is rich in bacteria and the moist passageway provides an ideal medium for growth thereof. Although the distance between the passageway in the housing and the patient can be several feet, bacterial migration to the patient can take place, particularly if a sterile male member has been installed a considerable time before the operation takes place.

According to one aspect of the present invention, a one-way valve is provided in the male valve member so that fluid cannot reach the fluid flow opening of the female member. The valve member can be easily used on existing units as described above. The existence of a second one-way valve has no adverse effect on operation and simply provides complete protection against bacterial contamination.

One particularly attractive and satisfactory way of providing such valve is to utilize a sleeve which preferably tapers and covers the opening of the second bore into the first bore. The sleeve, in fact, may simply be the end of the inlet tube which connects to the hand-held surgical aspirating device. When the pressure in the second bore exceeds the pressure in the first bore, due to a command for pressure relief, the sleeve is pushed aside by the air flow and the T coupling functions normally. However, when the pressure in the first bore exceeds the pressure in the second bore, the sleeve prevents any flow of fluid or gas into the second bore which could contaminate the fluid opening of the female member and the associated passage as noted above.

The male valve member described in the above patent is formed of a rigid base portion and a separate attached relatively resilient face portion. The cross-section of the male member in a plane transverse to the first bore extending therethrough is asymmetrical. The male member is installed by simply placing it in the cylindrical receptacle and rotating by finger pressure on an outwardly extending lever until the second bore, which extends through the resilient member, engages the fluid flow opening. The asymmetrical cross-section of the male member results in a locking of the male and female together in the proper position after rotation.

While generally satisfactory, the above-described male member has a number of drawbacks, in addition to the possible contamination problem discussed above. First, the member is formed in two separate parts which must be attached together leading to additional complexity in assembly and additional cost. The required asymmetrical configuration of the male member leads to additional expense. Although camming surfaces provide a "feel" when the male member has been rotated to its desired position, it is possible that full engagement may not take place unless the person installing the male member takes care to make sure that it is rotated to the full desired extent.

According to a further aspect of the present invention, the disposable male valve member is inserted and locked into place, not by rotation, but either by sliding movement along the direction in which the first bore extends or by simply pushing the male member in a linear direction until it properly engages with the female receptacle. In both instances, this is accomplished by providing at least part of the male member with resilient portions which are compressed when the male member is inserted and which provide a positive lock of the male and female members together with the second bore communicating with the fluid flow opening. Preferably, the entire valve member is formed of a resilient material, such as silane plastic, which can be easily formed as a unitary member, eliminating the need for any assembly and reducing expense of the device.

At least a portion, however, of the valve member which is inserted into the cylindrical receptacle is of resilient material and normally has dimensions greater than the dimensions of corresponding portions of the receptacle which contact the male portion when the male and female portions are in cooperation. Compression of the male portions upon insertion positively locks together the male and female members with the second bore communicating with the fluid flow opening.

In a first embodiment of the invention, the valve member includes a generally cylindrical portion adapted for insertion into the cylindrical receptacle. A plurality of resilient protrusions are provided adjacent each end and extending more than one-half around the circumference of this partially cylindrical part. These resilient portions contact and firmly lock together the male and female members as described above. In addition, a stop member is provided extending upwardly from the generally cylindrical portion for contacting the corresponding surface of the female member when the male member is properly in position with the second bore sealingly engaged with the fluid flow opening.

According to a second embodiment of the present invention, the male member is made entirely of resilient material and is tapered in the direction along which the first bore extends from a stop surface. The male member is simply inserted into the cylindrical receptacle of the female member and slid along the cylindrical receptacle in the direction in which the bore extends. The tapered material is thus compressed to lock together the male and female members with the stop surface contacting an associate stop surface of the female member when the second bore is sealingly engaged with the fluid flow opening.

Other objects and purposes of the invention will become clear from the following detailed description of the drawings.

DETAILED DESCRIPTION OF THE DRAWINGS

Figure 1:
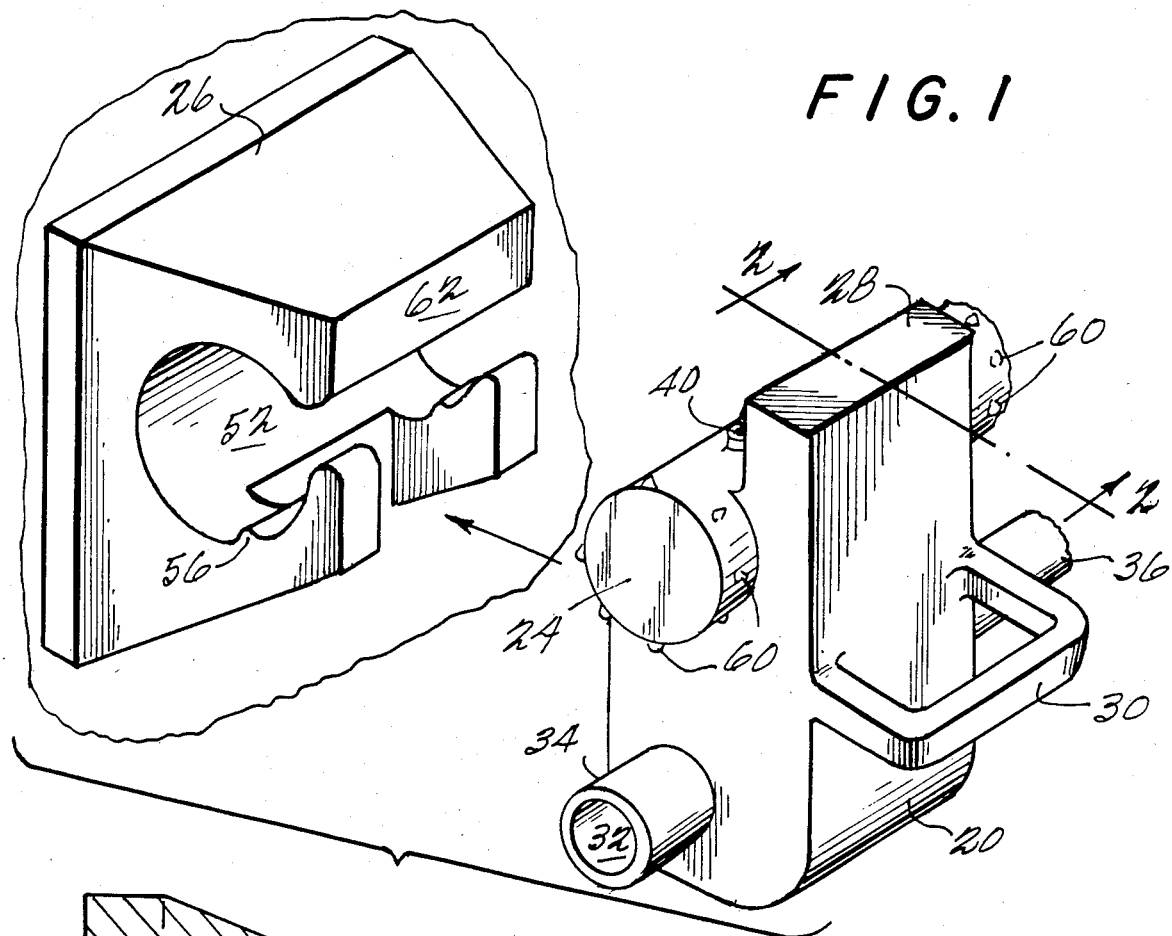
FIG. 1 shows a perspective view of one embodiment of the disposable male valve member of the present invention.
Figure 2:
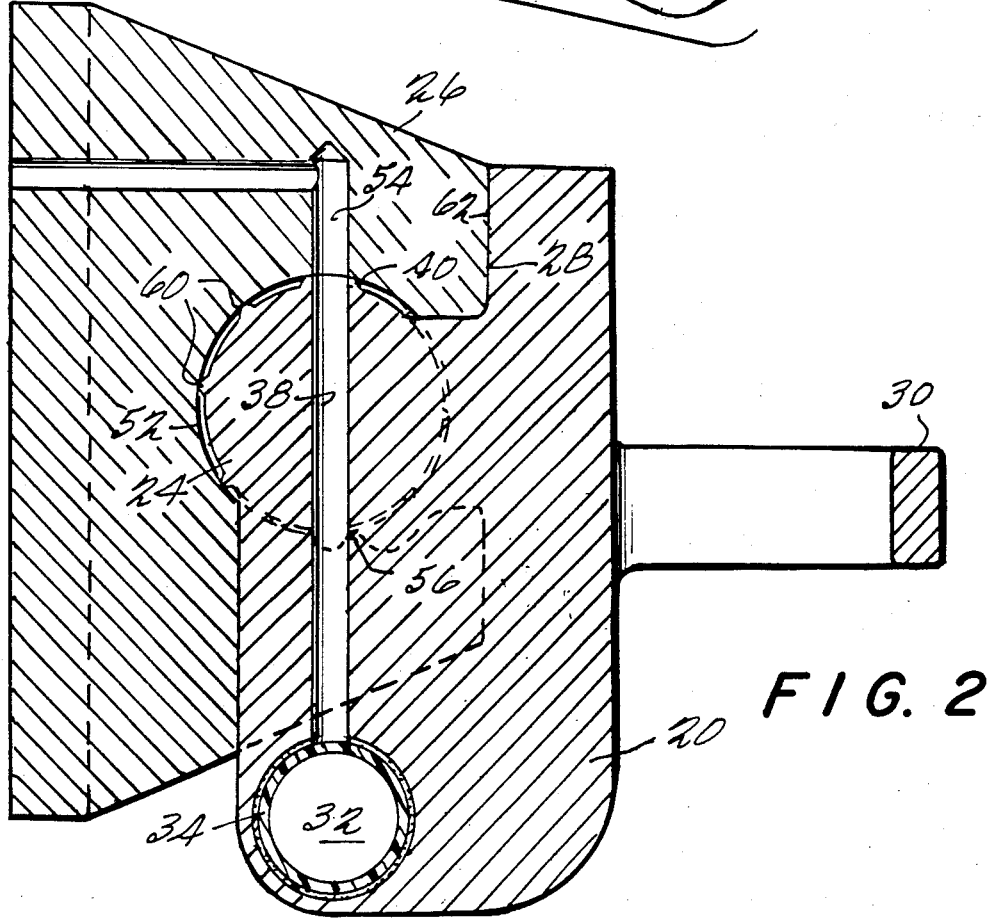
FIG. 2 shows a sectional view of the male and female members of FIG. 1 along lines 2-2'.
Figure 3:
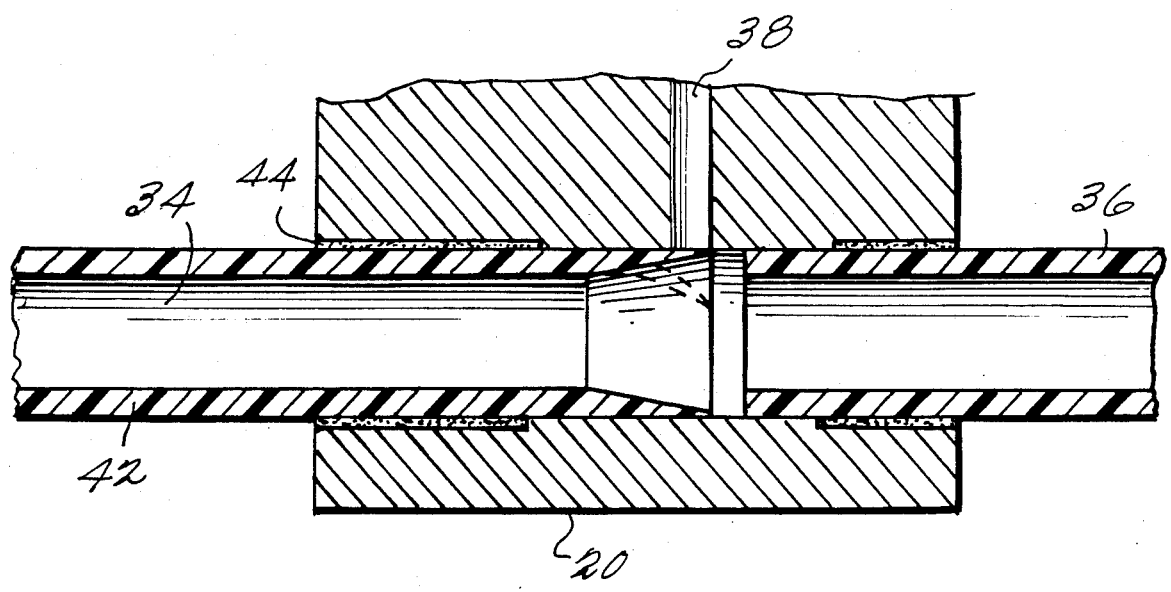
FIG. 3 shows a partial sectional view of the male member of FIG. 1.

Reference is now made to FIGS. 1 and 2 which illustrate a first embodiment of the present invention, and to FIG. 3 which illustrates a perspective view of the male and female members being coupled together.

Male member 20 is formed with a first part 24 adapted to be received within the generally cylindrical receptacle of the female member 26. Extending upwardly from part 24 is a stop part 28 which contacts a corresponding stop surface of the female member. Part 30 extends outwardly and provides surfaces for manually gripping the valve member 20 for insertion. Preferably, member 20 is integral and is formed of a resilient material such as silane plastic.

A first bore 32 extends through valve member 20 from an inlet indicated as 34 to an outlet indicated as 36. Inlet 34 is coupled to a hand-held surgical aspirating unit, while outlet 36 conveys fluid past a conventional peristaltic pump. A second bore 38 opens into the first bore 32 and communicates first bore 30 with a fluid flow opening of the female member receptacle. The portion of part 24 adjacent the opening of bore 38 is raised to form a boss 40 providing a sealing engagement with the fluid flow opening.

As can be best seen in FIG. 3, sleeve 42 extends into bore 32 through inlet 34 and preferably forms the tubing which connects to the hand-held unit (not shown). Sleeve 42 is bonded to member 20 at inlet 34 by a suitable adhesive layer 44 or otherwise as desired. The end of sleeve 42 within bore 32 is tapered and extends slightly beyond the opening of second bore 38 into first bore 32. When the pressure in bore 38 is greater than the pressure in bore 32, typically in response to a command to relieve pressure, the portion of sleeve 42 covering that opening is pushed aside and the unit functions as described above and as intended. However, when the pressure in bore 32 exceeds the pressure in bore 38, sleeve 42 forms a one-way valve which prevents any flow of fluid or gases into bore 38 and consequently any contamination with bacteria of that bore or any other passages which are coupled thereto.

Referring to FIG. 2, female member 26 is provided with a generally cylindrical receptacle 52 with a fluid flow opening 54 as described above opening into receptacle 52. Cam surfaces 56 are typically provided in such a female member as described in the above patent but are not important to the present invention. Such cam surfaces do not in any way interfere with proper installation or use of the male valve member of the present invention.

Valve member 20 is installed by manually gripping parts 30 and pushing the device inward. The protrusions 60, which can be best seen in FIG. 1, extend more than 180° around the circumference of the generally cylindrical part 24. These protrusions provide dimensions of part 24 which are greater than the corresponding dimensions in female receptacle 52. Therefore, when the male and female members are pushed together as shown, these protrusions compress to positively lock together the male and female members. Bore 38 will be sealingly engaged with fluid flow opening 54 when stop surface 28 contacts the corresponding surface 62 of female member 50.

Figure 4:
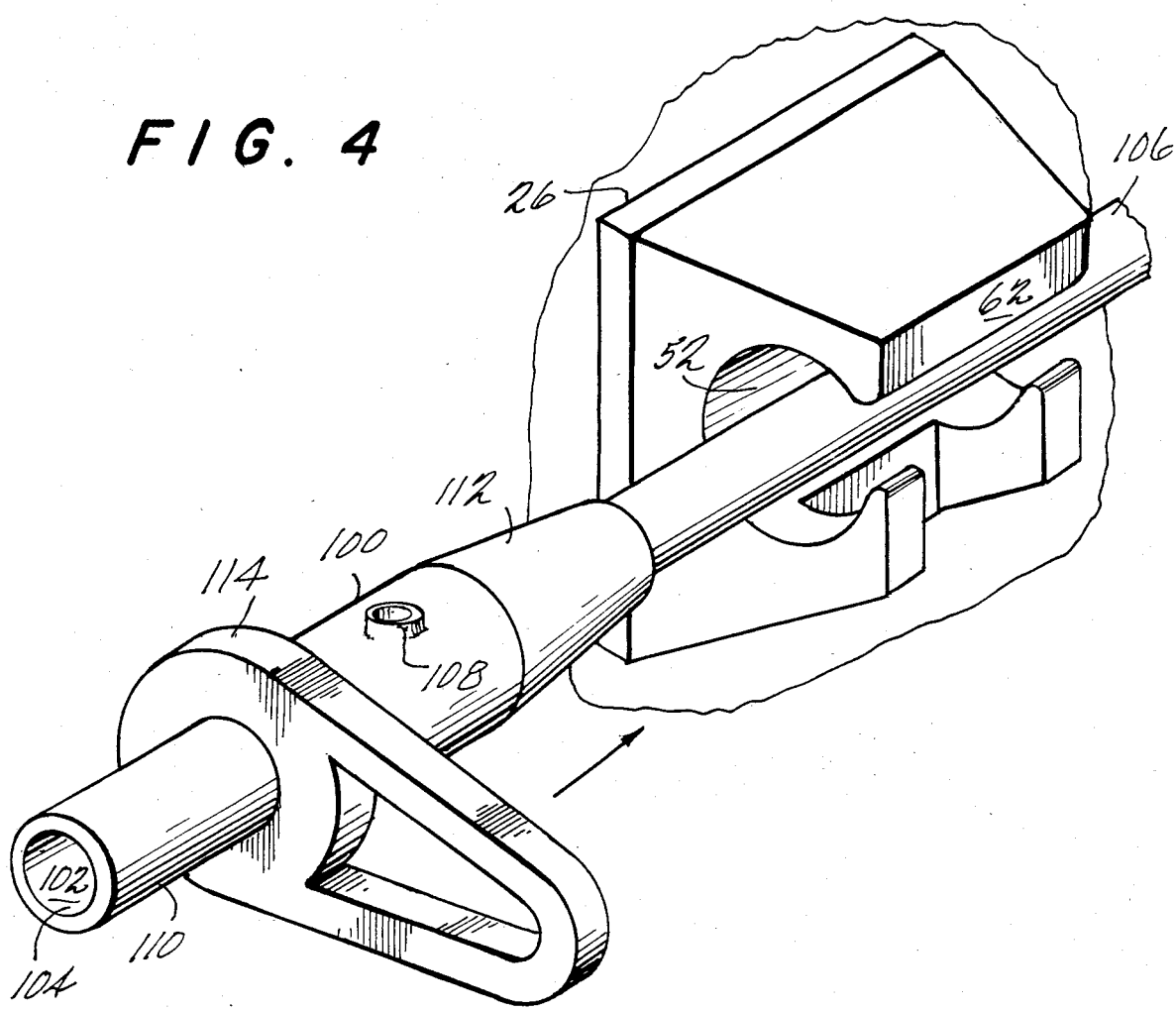
FIG. 4 shows a perspective view of a second embodiment of the valve member of the present invention.

FIG. 4 illustrates a second embodiment of the present invention. A resilient male member 100 is formed entirely of resilient material, for example, by molding, and is similarly provided with a first bore 102 extending between an inlet 104 and an outlet 106. A second bore 108 communicates first bore 102 with a fluid flow opening in the female member as shown in FIG. 3. Sleeve 110 is bonded to member 100 at inlet 104 in the same fashion as described above. Sleeve 110 is similarly tapered to cover the opening of bore 108 into bore 102 and functions exactly as described above.

The exterior surface of element 100 along the direction in which bore 102 extends is tapered, particularly in the area 112. Male member 100 can therefore be easily placed within the cylindrical receptacle 52 and slid from left to right, looking at FIG. 4, until the stop surface 114 contacts the associated stop surface of female member 26 at which time bore 108 will be engaged with fluid flow opening 54.

Many changes and modifications in the abovedescribed embodiment of the invention can of course be carried out without departing from the scope thereof. Accordingly, that scope is intened to be limited only by the scope of the appended claims.

What is claimed is:

1. A male valve member for cooperation with a female member to form a fluid coupling, said female member having a cooperating receptacle with a fluid flow opening to said receptacle comprising:

an element having a first bore extending therethrough from inlet to outlet and a second bore communicating said fluid flow opening with said first bore when said male member cooperates with said female member, said element having a first part with an exterior surface at least partially tapering from one end to the other along the direction in which said first bore extends and with said second bore opening onto said exterior surface, and a stop surface adjacent said one element end, said element being manually slidable in said receptacle along the direction in which said first bore extends and said stop surface contacts a corresponding surface of said female member to positively lock together said male and female members with said second bore communicating with said fluid flow opening, and one-way valve means mounted for permitting fluid flow from said fluid flow opening to said first bore through said second bore and preventing fluid flow from said first bore through said second bore to said fluid flow opening.

2. A member as in claim 1 wherein said element is integral and of resilient material.

3. A member as in claim 2 wherein said resilient material is silane plastic.

4. A valve member as in claim 1 wherein said coupling is a T coupling and said receptacle is generally cylindrical.

5. A member as in claim 1 wherein said one-way valve includes a sleeve of resilient material extending in said first bore and covering the opening of said second bore into said first bore adjacent one end of said sleeve so that fluid flows from said second bore into said first bore when the pressure in said second bore is greater than the pressure in said first bore and fluid is blocked from flowing from said first bore to said second bore when the pressure in said first bore is greater than the pressure in said second bore.

6. A member as in claim 1 wherein said sleeve is tapered adjacent said opening of said second bore into said first bore, extends outward from said first bore at said inlet to form an inlet tube and is bonded to said element where said sleeve enters said first bore.

7. A member as in claim 6 including an outlet tube extending into said first bore at the other end thereof to form an outlet tube.

8. A member as in claim 1 wherein said element includes at least a portion which is resilient and normally has dimensions greater than the dimensions of a corresponding portion of said receptacle which contact said element portion when said male and female members are in cooperation so that compression of said element portion upon insertion positively locks together said male and female members with said second bore communicating with said fluid flow opening.

9. A member as in claim 8 wherein said element has a raised part about the opening of said second bore into said stop part to seal the junction of said second bore opening and said fluid flow opening.

10. A member as in claim 9 wherein said element has a second part extending outwardly from said first part for manual engagement to slide said element.

11. A member as in claim 9 wherein said element is resilient so that portions of said exterior surface in contact with said receptable are compressed.

* * * * *